United States Patent
Quintanar

(10) Patent No.: US 12,233,196 B2
(45) Date of Patent: Feb. 25, 2025

(54) SYSTEMS AND METHODS FOR OPERATING A WOUND THERAPY DEVICE IN STEALTH MODE

(71) Applicant: T.J.Smith and Nephew, Limited, Hull (GB)

(72) Inventor: Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 93 days.

(21) Appl. No.: 17/785,650

(22) PCT Filed: Dec. 14, 2020

(86) PCT No.: PCT/EP2020/085975
§ 371 (c)(1),
(2) Date: Jun. 15, 2022

(87) PCT Pub. No.: WO2021/122454
PCT Pub. Date: Jun. 24, 2021

(65) Prior Publication Data
US 2023/0067636 A1   Mar. 2, 2023

(30) Foreign Application Priority Data
Dec. 17, 2019   (GB) ..................... 1918593

(51) Int. Cl.
*A61M 1/00* (2006.01)

(52) U.S. Cl.
CPC ............... *A61M 1/91* (2021.05); *A61M 1/98* (2021.05); *A61M 2205/502* (2013.01); *A61M 2205/581* (2013.01); *A61M 2205/583* (2013.01)

(58) Field of Classification Search
CPC .... A61M 1/91; A61M 1/98; A61M 2205/502; A61M 2205/581; A61M 2205/583
See application file for complete search history.

(56) References Cited

U.S. PATENT DOCUMENTS

| 2008/0200868 A1 | 8/2008 | Alberti et al. |
| 2013/0144227 A1* | 6/2013 | Locke ............. A61M 1/98 604/319 |

(Continued)

FOREIGN PATENT DOCUMENTS

| AU | 2014221257 A1 * | 9/2014 | ........ A61M 16/0003 |
| EP | 2647395 A1 | 10/2013 | |

(Continued)

OTHER PUBLICATIONS

International Preliminary Report on Patentability for Application No. PCT/EP2020/085975, mailed on Jun. 30, 2022, 9 pages.

(Continued)

*Primary Examiner* — Rebecca E Eisenberg
*Assistant Examiner* — Kate Elizabeth Strachan
(74) *Attorney, Agent, or Firm* — Knobbe, Martens, Olson & Bear, LLP

(57) ABSTRACT

A negative pressure wound therapy system can include a housing and a source of negative pressure enclosed by the housing configured to aspirate fluid from a wound covered by a wound dressing. The system can have one or more visual indicators visible at the exterior surface of the housing, configured to indicate status of the system to a user. The system can also have electronic circuitry enclosed by the housing, the electronic circuitry configured to automatically, or in response to a request from the user, transition the system between at least a first operational state and a second operational state, wherein in the second operational state the one or more visual indicators are configured to not emit any light or to emit light at one or more wavelengths that are not visible to naked human eye.

21 Claims, 6 Drawing Sheets

(56) References Cited

U.S. PATENT DOCUMENTS

| | | | |
|---|---|---|---|
| 2014/0318544 A1* | 10/2014 | Murphy | A61M 16/0875 |
| | | | 128/205.14 |
| 2015/0257925 A1 | 9/2015 | Schwartz | |
| 2019/0231939 A1* | 8/2019 | Askem | A61M 1/984 |
| 2019/0298899 A1* | 10/2019 | Hu | A61M 1/74 |
| 2020/0000980 A1* | 1/2020 | Quintanar | A61M 1/96 |
| 2020/0276367 A1* | 9/2020 | Seddon | A61M 1/96 |
| 2021/0001022 A1 | 1/2021 | Lin | |

FOREIGN PATENT DOCUMENTS

| | | | |
|---|---|---|---|
| WO | WO-2006133101 A2 * | 12/2006 | A61M 37/00 |
| WO | WO-2008036359 A2 | 3/2008 | |
| WO | WO-2008039223 A1 | 4/2008 | |
| WO | WO-2013136181 A2 | 9/2013 | |
| WO | WO-2016103031 A1 | 6/2016 | |
| WO | WO-2017087157 A1 | 5/2017 | |

OTHER PUBLICATIONS

International Search Report and Written Opinion for Application No. PCT/EP2020/085975, mailed on Mar. 24, 2021, 16 pages.

\* cited by examiner

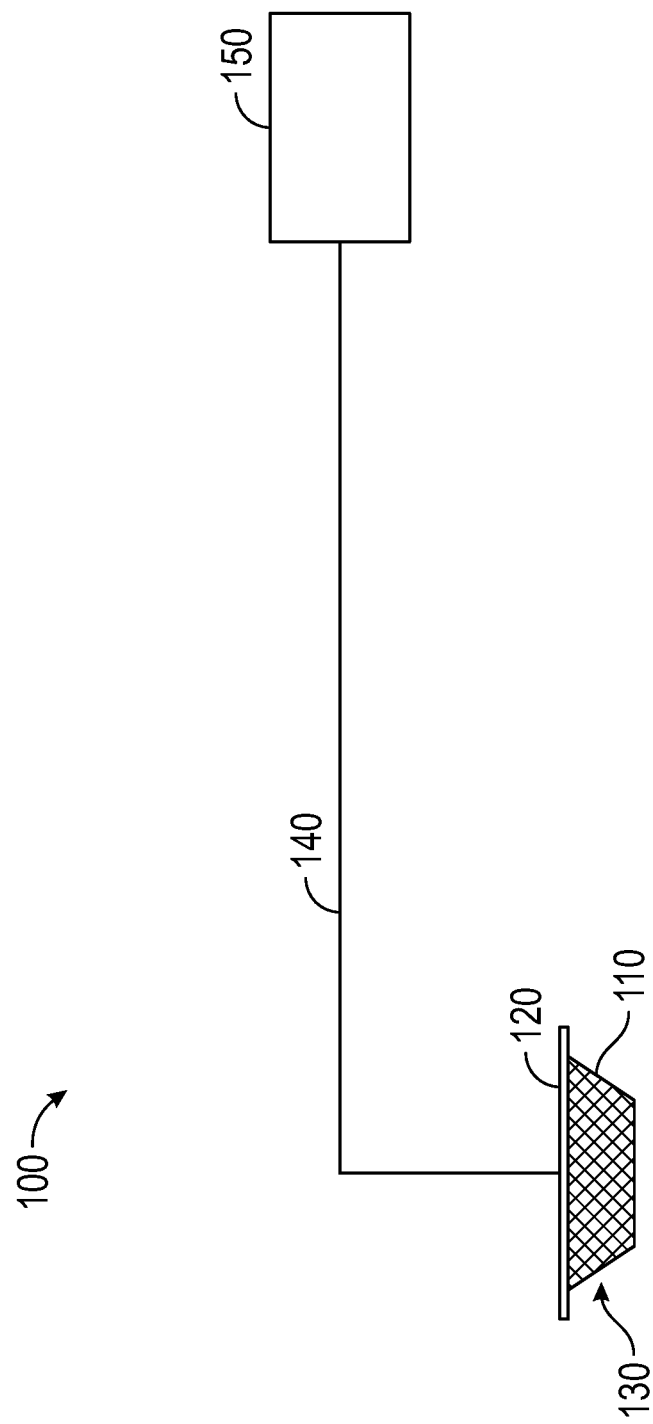

SYSTEMS AND METHODS FOR OPERATING A WOUND THERAPY DEVICE IN STEALTH MODE

PRIORITY CLAIM AND INCORPORATION BY REFERENCE

The present application is a U.S. national stage application of International Patent Application No. PCT/EP2020/085975, filed Dec. 14, 2020, which claims priority from GB Patent Application No. 1918593.3, filed on Dec. 17, 2019, titled SYSTEMS AND METHODS FOR OPERATING A WOUND THERAPY DEVICE IN STEALTH MODE, the contents of which application are hereby incorporated by reference herein in their entirety as if fully set forth herein. The benefit of priority is claimed under the appropriate legal basis including, without limitation, under 35 U.S.C. § 119 (e).

TECHNICAL FIELD

Arrangements described herein relate to apparatuses, systems, and methods the treatment of wounds, for example using dressings in combination with negative pressure wound therapy.

BACKGROUND

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds, and abdominal wounds or the like. TNP therapy assists in the closure and healing of wounds by reducing tissue edema, encouraging blood flow, stimulating the formation of granulation tissue, removing excess exudates and may reduce bacterial load. Thus, reducing infection to the wound. Furthermore, TNP therapy permits less outside disturbance of the wound and promotes more rapid healing. Existing TNP devices generate indications that are detectable by a user and third parties, which can be detrimental in situations when the user of the TNP device does not wish to be disturbed (such as, at night) or detected (such as, on a battlefield).

SUMMARY OF SOME EXEMPLIFYING ARRANGEMENTS

Disclosed herein are arrangements of a negative pressure wound therapy system, that can have a housing with an exterior surface, a source of negative pressure enclosed by the housing, the source of negative pressure configured to aspirate fluid from a wound covered by a wound dressing, one or more visual indicators visible at the exterior surface of the housing, and electronic circuitry enclosed by the housing. The electronic circuitry can be configured to transition between at least a first operational state and a second operational state automatically or in response to a request from the user. In any arrangements, in the second operational state, the one or more visual indicators can be configured to not emit any light or to emit light at one or more wavelengths that are not visible to naked human eye. Additionally, the one or more visual indicators can be configured to indicate status of the system to a user.

Also disclosed herein are arrangements of a negative pressure wound therapy system that can have a housing with an exterior surface, a source of negative pressure configured to provide a reduced pressure to a space between a wound and a wound dressing, and one or more visual indicators that can be configured to be visible at the exterior surface of the housing. The one or more visual indicators can be configured to indicate a status of the system to a user. In any arrangements disclosed here, the negative pressure wound therapy system can be configured such that, in at least one operational state, the one or more visual indicators emit light only at one or more wavelengths that are not visible to the naked eye.

Also disclosed herein are arrangements of a negative pressure wound therapy system that can have a housing with an exterior surface, a source of negative pressure configured to provide a reduced pressure to a space between a wound and a wound dressing, and one or more visual indicators visible at the exterior surface of the housing. In some arrangements, the one or more visual indicators can be configured to indicate status of the system to a user. Further, in some arrangements, the negative pressure wound therapy system can be configured such that, in at least one operational state, the one or more visual indicators emit light only at a wavelength that is not visible to the naked eye.

The systems of any of the preceding paragraphs and/or any of the apparatuses disclosed herein can include one or more of the following features, in any combination. In the second operational state, the one or more visual indicators can be configured to emit light at the one or more wavelengths that are not visible to the naked human eye but that are visible to a user using a night vision viewing device. In the first operational state, the one or more visual indicators can be configured to emit light that is visible to the naked human eye. In the second operational state, the system can be configured to not emit any visible light when the negative pressure wound therapy system is operating. Further, in any arrangements, the one or more visual indicators can be configured to be dimmed or be dimmable (such as, based on a level of ambient light). The electronic circuitry can be configured to transition between at least the first operational state and the second operational state in response to a single press of a button positioned at least partially on the exterior surface. Further, the system can be configured to automatically transition to the second state or automatically operate in the second state when the system is surrounded by darkness.

The system of any of the preceding paragraphs and/or any of the apparatuses disclosed herein can include one or more of the following features, in any combination. The electronic circuitry can be configured to transition between at least the first operational state and the second operational state in response to manipulation of at least one of a physical or a touchscreen-based button, a switch, a slider, or a dial positioned at least partially on the exterior surface. Further, the one or more visual indicators can be configured to emit infrared light in the second operational state. For example and without limitation, in any arrangements disclosed herein, the one or more visual indicators can be configured to emit light only at a wavelength that is 850 nm or greater, 940 nm or greater, or 1000 nm or greater in the second operational state. The system can further include one or more audible indicators configured to indicate the status of the system, which one or more audible indicators configured to be silent in the second operational state. Further, the one or more audible indicators can be configured to indicate the status of the system or to provide audible indication in the second operational state.

The system of any of the preceding paragraphs and/or any of the apparatuses disclosed herein can include one or more of the following features, in any combination. The system can further include one or more tactile indicators configured to indicate the status of the system in the second operational state, or one or more tactile indicators configured to indicate the status of the system, and/or one or more tactile indicators configured to provide tactile indication in the second operational state. Further, in the second operational state, the system can be configured to not transmit any communication data to a remote computing device. In any arrangements, the system can have a collection canister configured to be coupled with the housing, the collection canister being in communication with the source of negative pressure and being configured to collect exudate from a wound. The status can be related to the configuration, control, and/or operation of the system. The electronic circuitry can be configured to automatically transition to the second operational state in response to determining that the visible light surrounding the device is reduced to below a threshold level. The system can further include a wound dressing configured to be fluidically coupled with the source of negative pressure.

A negative pressure wound therapy system, having a housing with an exterior surface, a source of negative pressure configured to aspirate fluid from a wound covered by a wound dressing, one or more visual indicators visible at the exterior surface of the housing, the one or more visual indicators configured to indicate status of the system to a user, and electronic circuitry enclosed by the housing.

The system of any of the preceding paragraphs and/or any of the apparatuses disclosed herein can include one or more of the following features. The electronic circuitry can be configured to automatically or in response to a request from the user, transition from a first operational state in which the device emits light at a wavelength that is visible to the naked eye and a second operational state in which the device emits light only at a wavelength that is not visible to the naked eye.

A method of operating a negative pressure wound therapy device that can include activating the negative pressure wound therapy device that is coupled with a wound dressing so as to aspirate fluid from a wound covered by a wound dressing and changing the negative pressure wound therapy device to a second operational state in which one or more visual indicators of the negative pressure wound therapy device emit light at one or more wavelengths that are not visible to naked human eye but are visible using a night vision device, thereby permitting monitoring one or more operating parameters of the negative pressure wound therapy device while the negative pressure wound therapy device is in the second operational state by viewing the one or more indicators using the night vision viewing device. The night vision viewing device can be a pair of night vision goggles or a night vision scope.

A method of operating and/or using the apparatus of any of the preceding paragraphs and/or described herein is disclosed.

BRIEF DESCRIPTION OF THE DRAWINGS

FIG. 1 illustrates a reduced pressure wound therapy system.

DETAILED DESCRIPTION

Figure 2A:
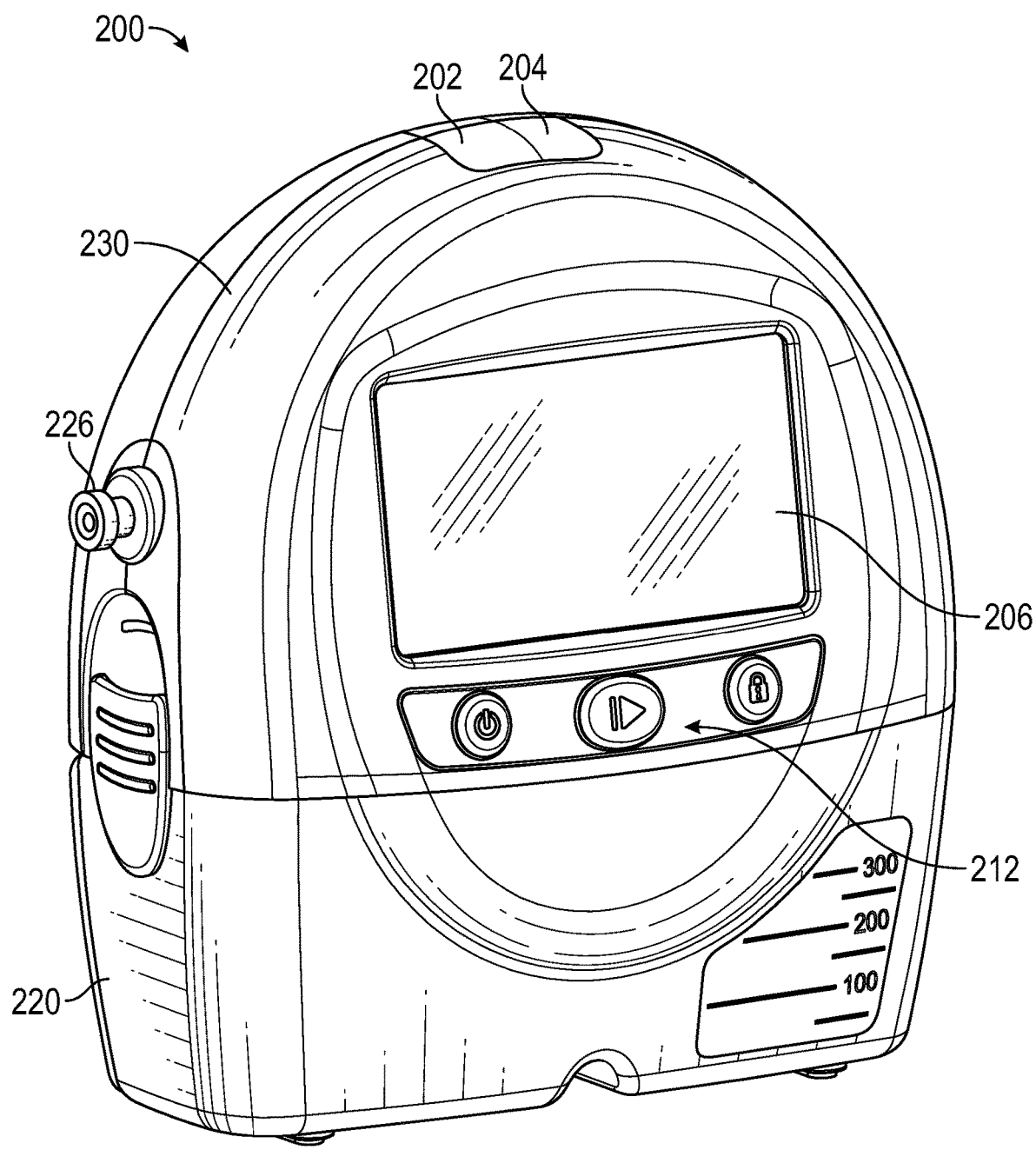
FIGS. 2A-2B illustrate a reduced pressure wound therapy device and canister.

Any of the features, components, or details of any of the arrangements or arrangements disclosed in this application, including without limitation any of the apparatus arrangements and any of the negative pressure wound therapy (also referred to herein as reduced pressure wound therapy or treatment or negative pressure wound treatment) arrangements disclosed herein, are interchangeably combinable with any other features, components, or details of any of the arrangements or arrangements disclosed herein to form new arrangements and arrangements.

Arrangements disclosed herein relate to systems and methods of monitoring and/or treating a wound. It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment (also referred to as negative pressure treatment). A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Arrangements of systems and methods disclosed herein can be used with topical negative pressure ("TNP") or reduced pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat and/or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

A typical human eye can respond to wavelengths of light from about 390 nm to about 750 nm (nanometres). Outside of this range, the ability of the human eye to see light falls away sharply. Infrared light in about the 850 nm wavelength is difficult for many to see with the naked human eye.

There are generally understood to be three different types of infrared light: near-infrared (near-IR) light, mid infrared (mid-IR) light, and thermal-infrared (thermal-IR) light. Near-infrared (near-IR) is the closest type of infrared light to visible light. Near-IR light typically has wavelengths that range from 0.7 to 1.3 microns (i.e., 700 billionths to 1,300 billionths of a meter). Mid-infrared (mid-IR) typically has wavelengths ranging from 1.3 to 3 microns. Both near-IR and mid-IR can be used by a variety of electronic devices, including remote controls to communicate signals. Thermal-infrared (thermal-IR) occupies the largest part of the infrared spectrum. Thermal-IR has wavelengths ranging from 3 microns to more than 30 microns.

Human vision is understood to occur in the photoreceptor layer of the eye. This layer has the specialized cells known as the photoreceptors (comprised of rods and cones), which are responsible for converting the light striking them into electrochemical nerve pulses. The rods and cones process electromagnetic radiation with wavelengths in the 750 nanometers (nm) (red) to 400 nm (violet) range, which is what we consider the visible spectrum of light.

Night-vision viewing devices, such as but not limited to goggles and scopes, can be used to view light at wavelengths that are above the wavelength that is visible to the naked eye. Night-vision viewing devices have many useful applications, including, for example and without limitation, military operations, law enforcement, hunting, wildlife observations, and surveillance. To remain hidden and difficult to detect by the human eye, a user engaging in such operations may wish to avoid wearing any devices or carrying any devices that emit visible light.

The use of negative pressure wound therapy devices can be useful in treating personnel in combat zones, and can be used by other persons in a range of applications, including, for example and without limitation, military operations, law enforcement, hunting, wildlife observations, and surveillance. To remain hidden and difficult to detect by the human eye, a user engaging in such applications may wish to avoid wearing any devices or carrying any devices that emit visible light. Therefore, to enable a user of a negative pressure wound therapy device that is engaged in such applications to remain less detectable, or for any other suitable reason, any arrangements of the negative pressure wound therapy devices disclosed herein can be configured to operate without emitting any visible or detectable light, audible sound, wireless or wired communication, and/or the like, or to be changeable to an operational state, such as a second operational state as described below, in which the negative pressure wound therapy device does not emit any visible or detectable light, audible sound, wireless or wired communication, and/or the like. Additionally or alternatively, such operation or operational state can be advantageous in situations where the user does not wish to be disturbed, such as at night, during period of rest, or the like.

Negative Pressure System

FIG. 1 illustrates a negative or reduced pressure wound treatment (or TNP) system 100 having a reduced (or negative) pressure wound therapy device 150 and a wound cover 120, which can provide a substantially or completely air tight cover over a wound. The TNP system 100 can, in some arrangements, have a wound filler 130 placed inside a wound cavity 110. The wound filler 130 in combination with the wound cover 120 can be referred to as wound dressing. In some arrangements, however, the wound dressing can have a wound cover without a wound filler. A single or multi lumen tube or conduit 140 can be connected the wound cover 120 with a reduced (or negative) pressure wound therapy device 150 configured to supply reduced pressure. The wound cover 120 can be in fluidic communication with the wound cavity 110. With any of the systems disclosed herein, as is illustrated in FIG. 1, a negative pressure wound therapy device (sometimes as a whole or partially referred to as a "pump assembly") can be a canisterless (meaning that exudate is collected in the wound dressing or is transferred via tube 140 for collection to another location). However, any of the pump assemblies disclosed herein can be configured to include or support a canister. Additionally, with any of the systems disclosed herein, any of the pump assemblies can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. In some cases, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material. The wound cover 120 can have a port (not shown) configured to receive an end of the conduit 140. In some cases, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway or path between the device (also referred to herein as pump assembly) 150 and the wound cover 120, so as to supply the reduced pressure provided by the device 150 to wound cavity 110.

The wound cover 120 and the wound filler 130 can be provided as a single article or an integrated single unit. In some cases, no wound filler is provided and the wound cover by itself may be considered the wound dressing. The wound dressing may then be connected, via the conduit 140, to a source of negative pressure, such as the pump assembly/device 150. In some cases, though not required, the pump assembly/device 150 can be miniaturized and portable, although larger conventional pumps such can also be used.

The wound cover 120 can be located over a wound site to be treated. The wound cover 120 can form a substantially sealed cavity or enclosure over the wound site. In some cases, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some cases, the components of the TNP system described herein can be particularly suited for incisional wounds that exude a small amount of wound exudate.

The system can be designed to operate without the use of an exudate canister. The system can be configured to support an exudate canister. In some cases, configuring the pump assembly/device 150 and tubing 140 so that the tubing 140 can be quickly and easily removed from the pump assembly/device 150 can facilitate or improve the process of dressing or pump changes, if necessary. Any of the pump assemblies disclosed herein can be configured to have any suitable connection between the tubing and the pump.

The pump assembly/device 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively a pressure range of up to −75 mmHg, up to −80 mmHg or over −80 mmHg can be used. Also in some cases a pressure range of below −75 mmHg can be used. Alternatively a pressure range of over approximately −100 mmHg, or even 150 mmHg, can be supplied by the pump assembly/device 150.

The pump assembly/device 150 can be configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some cases, switching between low and high set points and vice versa can be performed according to a step waveform, square waveform, sinusoidal waveform, and the like.

In operation, the wound filler 130 can be inserted into the wound cavity 110 and wound cover 120 can be placed so as to seal the wound cavity 110. The pump assembly/device 150 can provide a source of a negative pressure to the wound cover 120, which can be transmitted to the wound cavity 110 via the wound filler 130. Fluid (such as, wound exudate) can be drawn through the conduit 140, and can be stored in a canister. In some cases, fluid is absorbed by the wound filler 130 or one or more absorbent layers (not shown).

Wound dressings that may be utilized with the pump assembly and systems of the present application include Renasys-F, Renasys-G, Renasys AB, and Pico Dressings available from Smith & Nephew. Further description of such wound dressings and other components of a negative pressure wound therapy system that may be used with the pump assembly and systems of the present application are found in U.S. Patent Publication Nos. 2012/0116334, 2011/0213287, 2011/0282309, 2012/0136325 and U.S. Pat. No. 9,084,845, each of which is incorporated by reference in its entirety. In some cases, other suitable wound dressings can be utilized.

Pump Assembly and Canister

Figure 2B:
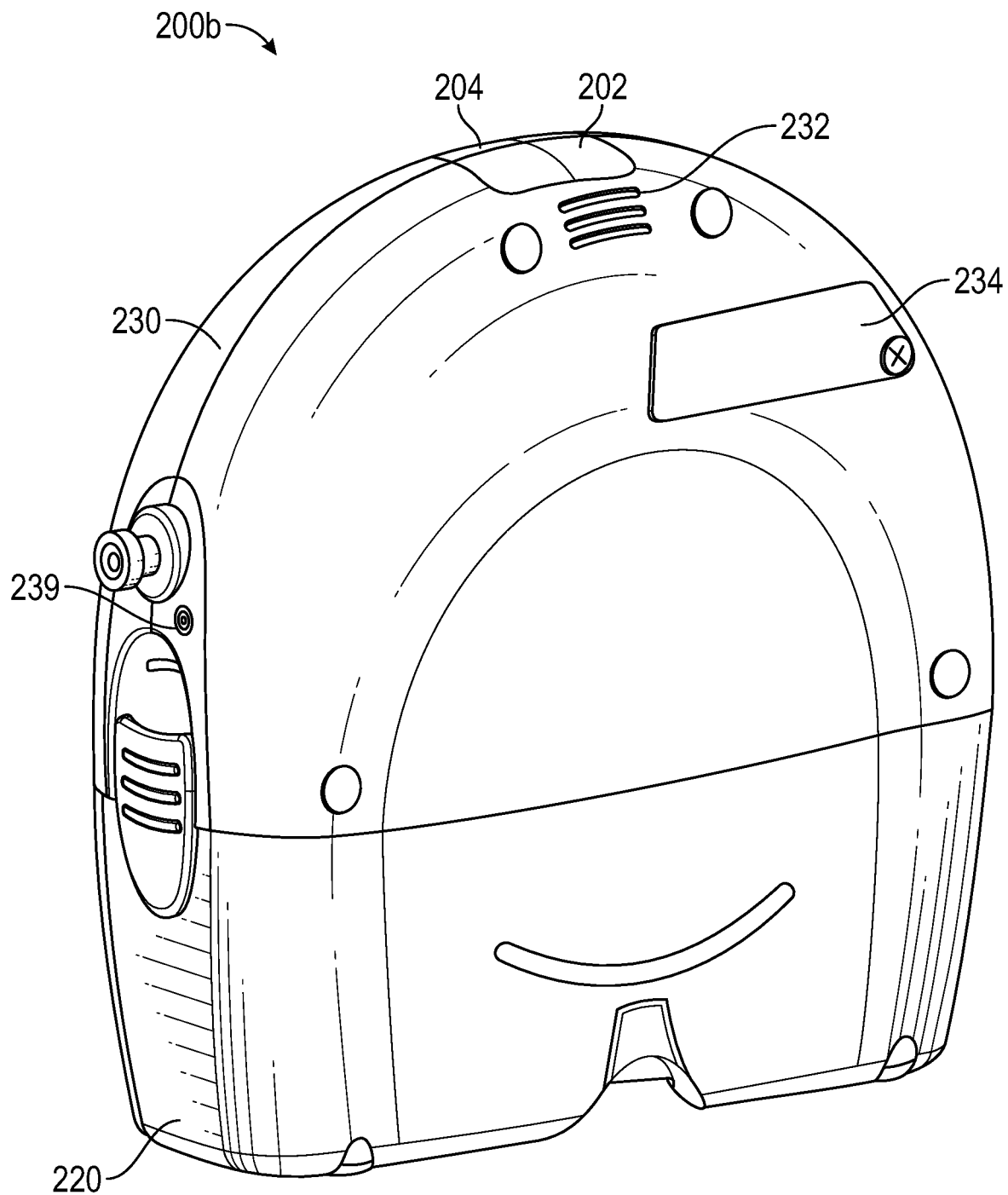

FIGS. 2A-B illustrate a negative pressure wound therapy device 200 including a pump assembly 230 and a canister 220. As is illustrated, the pump assembly 230 and the canister are connected, thereby forming the device 200.

Indicators

Any of the arrangements of the pump assemblies disclosed herein, including without limitation pump assembly/device 150, can have one or more indicators on a housing of such device. Further, any negative pressure wound therapy systems disclosed herein can have one or more indicators on the dressing or wound cover of the system, in addition to or in the alternative to, one or more indicators on the housing of the device or otherwise. Such one or more indicators can include a visual indicator 202 that can be, for example, configured to indicate alarms and a visual indicator 204 that can be, for example, configured to indicate a status of the TNP system. The indicators 202 and 204 can be configured to alert a user (for example, patient, health care provider, or the like) to a variety of operating and/or failure conditions of the system, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof.

In some cases, the pump assembly 230 can comprise additional indicators. In some cases, a single indicator is used. In some cases, multiple indicators are used.

As described herein, any one or more indicators can be used to provide visual, audio, and/or tactile indications or indications related to wired or wireless communications. One or more indicators can include visual indicators (such as 202, 204, 414), a display (such as, 206) that can include a plurality of indicators, keys or buttons (such as, 212 or 416), speaker (such as, 232), communications device (such as, 330, 340), or the like. For example, the indicator 202 can be configured to signal alarm conditions, such as canister full, power low, conduit 140 disconnected, seal broken in the wound seal 120, and so on. The indicator 202 can be configured to display red flashing light to draw user's attention. As another example, the indicator 204 can be configured to signal status of the TNP system, such as therapy delivery is ok, a leak is detected, a level of reduced pressure under the wound dressing, battery level, and so on. The indicator 204 can be configured to display one or more different colors of light, such as green, yellow, etc. For example, green light can be emitted when the TNP system is operating properly and yellow light can be emitted to indicate a warning. As yet another example, audio indicator, such as speaker 232 (illustrated in FIG. 2B) can be used to generate an acoustic alarm in response to deviations in therapy delivery, non-compliance with therapy delivery, or any other similar or other operating conditions or combinations thereof.

Display Screen

In any arrangements disclosed herein, the device can have a display or screen (such as display 206) that can be mounted in a recess formed in a case of the pump assembly. In some cases, the display 206 can be a touch screen display. In some cases, the display 206 can support playback of audiovisual (AV) content, such as instructional videos. The display 206 can be configured to render a number of screens or graphical user interfaces (GUIs) for configuring, controlling, and monitoring the operation of the TNP system such as when the device is in a particular operational state, for example a first operational state. The device can be configured such that the display does not emit any light at wavelengths that are visible to the human eye (naked or assisted by a night vision device) when the device is in a second operational state.

The pump assembly 230 can comprise a gripping portion formed in the case of the pump assembly. The gripping portion can be configured to assist the user to hold the pump assembly 230, such as during removal of the canister 220. The pump assembly 230 includes one or more strap mounts for connecting a carry strap to the pump assembly 230 or for attaching a cradle. In some cases, the canister 220 can be replaced with another canister, such as when the canister 220 has been filled with fluid.

The pump assembly 230 comprises one or more keys or buttons 212 configured to allow the user to operate and monitor the operation of the TNP system. As is illustrated, there can be a plurality of buttons. One button can be configured as a power button to turn on/off the pump assembly 230. Another button can be configured as a play/pause button for the delivery of negative pressure therapy. For example, pressing the button can cause therapy to start, and pressing the button afterward can cause therapy to pause or end. A button can be configured to lock the display 206 and/or the buttons 212. For instance, a button can be pressed so that the user does not unintentionally alter the delivery of the therapy. In some cases, multiple key presses and/or sequences of key presses can be used to operate the pump assembly 230. One of these buttons or an additional button or switch can be used to change the operational state of the device. As described herein, any of the buttons or other user interface elements described herein can be used to cause the pump assembly to transition from the first operational state into the second operational state or vice versa. In some cases, a single button press or interaction with another user interface element can cause the pump assembly to transition into the second operational state or cause the pump assembly to transition back to the first operational state. This can allow the user to quickly transition between different operational states.

The canister 220 is configured to hold fluid (such as, exudate) removed from the wound cavity 110. The canister 220 can include one or more latches for attaching the canister to the pump assembly 230. The exterior of the canister 220 can formed from frosted plastic so that the canister is substantially opaque and the contents of the canister and substantially hidden from plain view. The canister 220 includes a substantially transparent window, which can also include graduations or markings of level of volume. For example, the illustrated 300 mL canister 220 can include graduations of 50 mL, 100 mL, 150 mL, 200 mL, 250 mL, and 300 mL. In some cases, the canister can hold different volume of fluid and can include different graduation scale. The canister 220 comprises a tubing channel for connecting to the conduit 140.

FIG. 2B illustrates a rear view 200B of the pump assembly 230 and canister 220. The pump assembly 230 comprises the speaker 232 for producing sound. The speaker 232 can be used to generate an acoustic alarm in response to deviations in therapy delivery, non-compliance with therapy delivery, or any other similar or suitable conditions or combinations thereof. The speaker 232 can be used to generate audio feedback to user input.

The pump assembly 230 can include a filter access door 234 for accessing and replacing one or more filters, such as antibacterial filters. The pump assembly 230 can comprise a power jack 239 for charging and recharging an internal battery of the pump assembly. In some cases, the power jack 239 is a direct current (DC) jack. In some cases, the pump assembly can comprise a disposable power source, such as batteries, so that no power jack is needed. In some cases, one of the power supplies (primary) can deliver power to operate and control the pump. In some cases, a secondary power source can deliver power to one or more of the user interface, alert system, and/or communication system for uploading usage data to the cloud or communicating data to a remote computing device or computer. Remote computing device can be any one or more computing devices with at least one processor and/or database, such as one or more cloud servers (sometimes referred to as "the cloud"), one or more mobile phones, one or more tablets, one or more laptops, one or more computers, one or more other negative pressure wound therapy devices, or the like.

Stealth Mode

In any arrangements of the devices disclosed herein, including without limitation the device 150, the device can be configured such that the device does not emit any sounds, lights or visible indicators, communications signals such as wired or wireless signals, and/or other signals or indicators (or any combination of the foregoing) that may attract the attention or be detectable (such as, without limitation, to another person) when the negative pressure wound therapy device is changed to a stealth type operational state, such as in the second operational state described in more detail below. For example and without limitation, in any of the arrangements disclosed herein, the device can have one or more visual indicators visible on an exterior surface of a housing of the device configured to indicate at least a status of the device and/or a status of a level of negative pressure provided by the source of negative pressure, wherein the one or more (or, optionally, all) indicators can be configured to emit light at a wavelength that is above or below a wavelength that is visible to the naked eye, visible with assistance of the night vision viewing device (such as, night vision googles, or the like). The one or more indicators can be configured to emit light at a wavelength that is not visible to the naked eye but which is visible to a user using the night vision viewing device. The status indicated by any of the indicators described herein can be related to, without limitation, the configuration, control, and/or operation of the device.

Additionally or alternatively, in any of the negative pressure wound therapy device arrangements disclosed herein, including without limitation the device 150 or 400, the device can be configured to be changeable between at least the first operational state and the second operational state, in which the one or more indicators can be configured to not emit light, sound, data communication, or the like that may be detectable by the user or third party. Any arrangements of the devices disclosed herein can be configured such that any feature or component of the device that emits light (such as the one or more indicators, or a display, etc.) can be dimmable (such as, based on a level of ambient light).

Some arrangements of the negative pressure wound therapy device can be configured to be changeable between at least the first operational state and the second operational state with a press of a single button, by using at least one of a physical or a touchscreen based button, a switch, a slider, and a dial, or suitable feature or component designed to receive an input or command from a user to control an operating parameter of the device. Additionally or alternatively, the device can be configured to automatically change to the second state or automatically operate in the second operational state when the visible light surrounding the device is detected to be below a threshold level, such as when it gets dark outside or when the device is surrounded by darkness. The device can be configured to automatically change to the first state when the visible light is detected to be above the threshold level, such as when the sun rises. A sensor, such as a light sensor (also referred to as an ambient light sensor), can detect or monitor the state of visible light. In some arrangements, the light sensor can also be used to detect the brightness of ambient light to automatically adjust the display brightness (in one or both of the visible light wavelengths and for wavelengths of light that are not visible to the naked eye). This can allow for a combination of device discretion (for example, reducing an intensity of the light emitted by the one or more indicators in darker conditions) and good visibility in high ambient light conditions (for example, by increasing the intensity of emitted light). Additionally or alternatively, the device can keep track of local time, which can be used for transitioning to the first or second operational state.

In any arrangements disclosed herein, the one or more visual indicators can be configured to not emit light or to emit light at a wavelength that is below or above a wavelength that is visible to the naked human eye or human eye armed with the night vision viewing device (sometimes referred to as nonvisible light), at least when the negative pressure wound therapy device is in the second operational state. In other words, any devices can be configured to emit nonvisible light (through the one more indicators, or otherwise) in any operational state of the device, including the first and second operational states. In these configurations, the device can emit visible light in addition to nonvisible light in a first operational state, for example, and then turn off or modify operation of any visible light emitters when the device is changed to the second operational state. Other arrangements can be configured such that the device emits nonvisible light only in particular operational states, such as without limitation the second operational state. Other arrangements can be configured such that the device emits only nonvisible light in all operational states.

In some arrangements, the negative pressure wound therapy device can have a housing with an exterior surface, a source of negative pressure configured to aspirate fluid from a wound covered by a wound dressing, and one or more indicators visible on the exterior surface of the housing configured to indicate at least a status of the device and/or a status of a level of negative pressure provided by the source of negative pressure. The device can be configured to be switchable from a first operational state in which the device emits visible light and a second operational state in which the device emits light only nonvisible light.

In any arrangements disclosed herein, the nonvisible light can include infrared light, or light having a wavelength that is approximately 750 nm or greater, or greater than 750 nm, or that is approximately 840 nm or greater, or that is approximately 940 nm or greater, or that is approximately 1,000 nm or greater, or from greater than 750 nm to approximately 1,300 nm, or from approximately 840 nm to approximately 950 nm. Any of the devices disclosed herein can be configurable to allow a user to select a wavelength of the light emitted from the device from two or more different wavelengths of light, including two or more nonvisible wavelengths of light.

Any of the arrangements of the devices or systems disclosed herein, including, without limitation, the device 150 or 400, can have one or more audible indicators configured to indicate at least a status or an alert state of the device and/or a status of a level of negative pressure provided by the source of negative pressure. The device can be configured such that the one or more audible indicators are silent or non-audible when the negative pressure wound therapy device is in the second operational state. Similarly, any of the arrangements of the devices or systems disclosed herein, including, without limitation, device 150 or 400, can have one or more vibratory indicators configured to indicate at least a status or an alert state of the device and/or a status of a level of negative pressure provided by the source of negative pressure. Such vibratory indicators can be configured to be operational when the device is only in the second state, or, alternatively, when the device is in any operational state. Further, any arrangements of the devices disclosed herein can be configured such that the device does not emit any communications signals, such as wired or wireless signals, when the negative pressure wound therapy device is in a particular operational state, including without limitation the second operational state. In any arrangements, the device can be configurable by a user of the device so that the user can determine the operational mode of the particular features of the device (including the one or more indicator lights, the audible indicators, and/or the vibratory indicators) in any of the operational states of the device. For example, in the second operational mode, audible or tactile indicators may be used to provide indication of the device operation while one or more visual indicators are turned off or are configured to emit only nonvisible light.

Any of the system or device arrangements disclosed herein can have a collection canister coupled with the housing, the collection canister being in communication with the source of negative pressure and being configured to collect exudate from a wound. Any of the devices disclosed herein can have electronic circuitry configured at least to control the source of negative pressure and the one or more indicators.

Any of the arrangements of the devices and/or systems disclosed herein can be operated by performing any combination of the following steps: activating the negative pressure wound therapy device that can be coupled with a wound dressing so as to aspirate fluid from a wound covered by the wound dressing with the negative pressure wound therapy device and changing the negative pressure wound therapy device to second operational state in which one or more indicators of the negative pressure wound therapy device do not emit light or emit nonvisible light. In some cases, any other indicators, such as audible, tactile, or communication devices can be configured to not emit or transmit sound, vibration, or communication data in the second operational mode as described herein. In some cases, and the steps can include monitoring one or more operating parameters of the negative pressure wound therapy device while the negative pressure wound therapy device is in the second operational state by viewing the one or more indicators using a night vision viewing device. The night vision viewing device in any arrangement described herein can be a pair of night vision goggles, a night vision scope, or any other low light or night viewing device.

Control System

Figure 3:
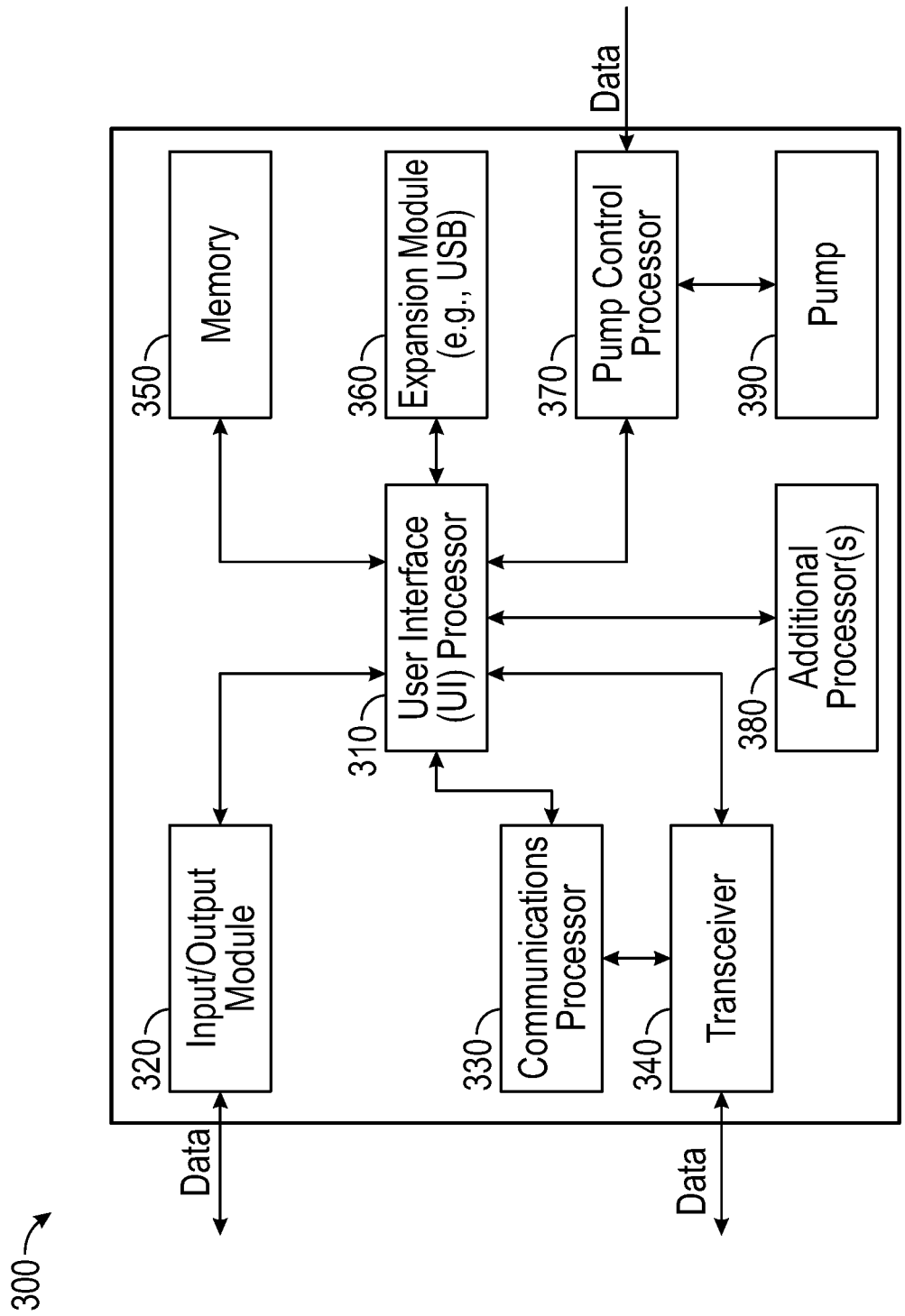
FIG. 3 illustrates a schematic of a reduced pressure wound therapy device.

FIG. 3 illustrates a schematic of a control system 300 which can be employed in any of the arrangements of wound monitoring and/or treatment systems described herein, such as in the device 200 of FIGS. 2A-2B. Electrical components can operate to accept user input, provide output to the user, operate the negative pressure source of a TNP system, provide network connectivity, and so on. It may be advantageous to utilize multiple processors in order to allocate or assign various tasks to different processors. In some cases, a first processor can be responsible for user activity and a second processor can be responsible for controlling another device, such as a pump 390. This way, the activity of controlling the other device, such as the pump 390, which may necessitate a higher level of responsiveness (corresponding to higher risk level), can be offloaded to a dedicated processor and, thereby, will not be interrupted by user interface tasks, which may take longer to complete because of interactions with the user.

Input and output to the other device, such as a pump 390, one or more sensors (for example, one or more pressure sensors configured to monitor pressure in one or more locations of the fluid flow path), or the like, can be controlled by an input/output (I/O) module 320. For example, the I/O module can receive data from one or more sensors through one or more ports, such as serial (for example, I2C), parallel, hybrid ports, and the like.

The processor 310 can also receive data from and provide data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, can store data in one or more memory modules 350, which can be internal and/or external to the processor 310. Any suitable type of memory can be used, including volatile and/or non-volatile memory, such as RAM, ROM, magnetic memory, solid-state memory, Magnetoresistive random-access memory (MRAM), and the like.

In some cases, the processor 310 can be a general purpose controller, such as a low-power processor. In other cases, the processor 310 can be an application specific processor. In some cases, the processor 310 can be configured as a "central" processor in the electronic architecture of the system 300, and the processor 310 can coordinate the activity of other processors, such as a pump control processor 370, communications processor 330, and one or more additional processors 380. The processor 310 can run a suitable operating system, such as a Linux, Windows CE, VxWorks, etc.

The pump control processor 370 (if present) can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. In some cases, the pump control processor 370 can measure pressure in a fluid flow path, using data received from one or more pressure sensors, calculate the rate of fluid flow, and control the pump. In some cases, the pump control processor 370 controls the pump motor so that a desired level of negative pressure in achieved in the wound cavity 110. The desired level of negative pressure can be pressure set or selected by the user. The pump control processor 370 can control the pump (for example, pump motor) using pulse-width modulation (PWM). A control signal for driving the pump can be a 0-100% duty cycle PWM signal. The pump control processor 370 can perform flow rate calculations and detect alarms. The pump control processor 370 can communicate information to the processor 310. The pump control processor 370 can include internal memory and/or can utilize memory 350. The pump control processor 370 can be a low-power processor.

A communications processor 330 can be configured to provide wired and/or wireless connectivity. The communications processor 330 can utilize one or more transceivers 340 for sending and receiving data. The one more transceivers 340 can include one or more antennas, optical sensors, optical transmitters, vibration motors or transducers, vibration sensors, acoustic sensors, ultrasound sensors, or the like. In some cases, the communications processor 330 can provide one or more of the following types of connections Global Positioning System (GPS), cellular connectivity (for example, 2G, 3G, LTE, 4G, 5G, or the like), near field communication (NFC), Bluetooth connectivity, radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software and/or firmware, pairing, and the like.

Any of the negative pressure wound therapy devices described herein can include one or more features disclosed in U.S. Pat. No. 9,737,649 or U.S. Patent Publication No. 2017/0216501, each of which is incorporated by reference in its entirety.

Canisterless Pump Assembly

Figure 4B:
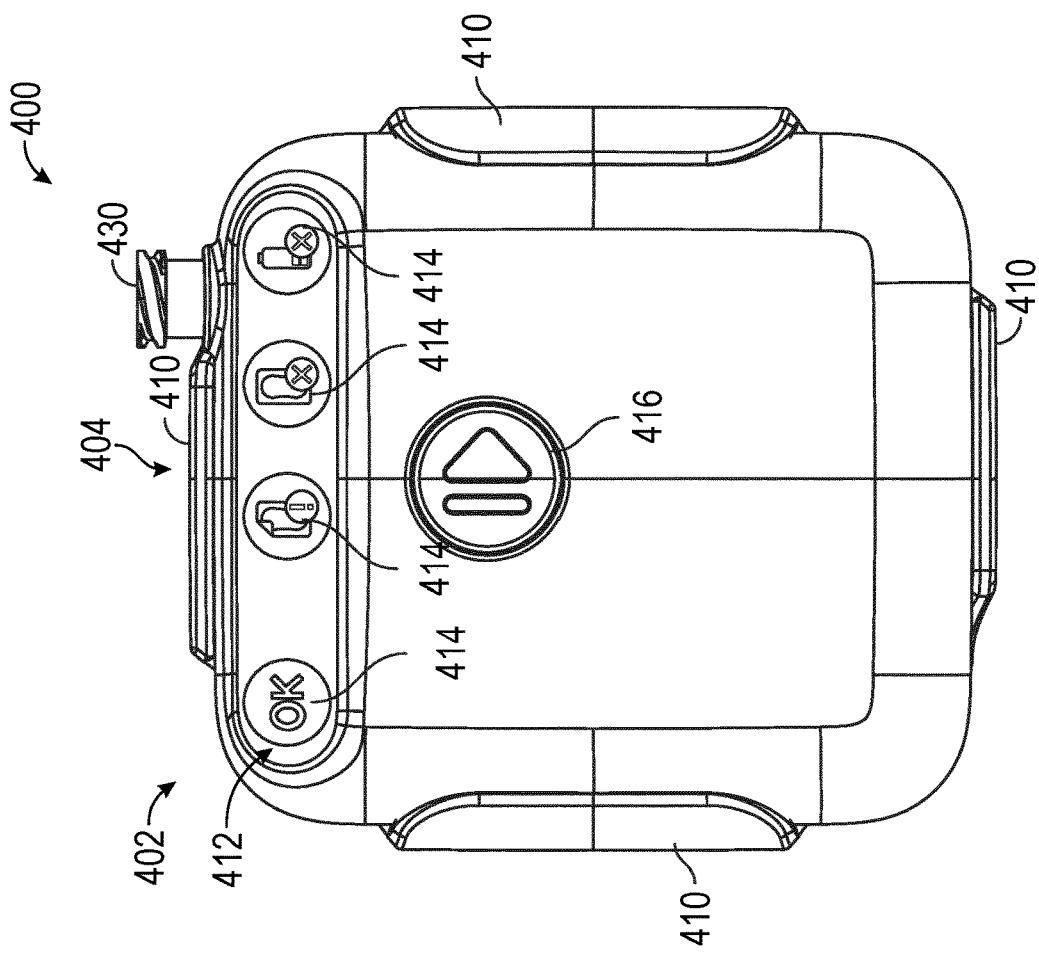
FIGS. 4A-4C illustrate a reduced pressure wound therapy device.
Figure 4A:
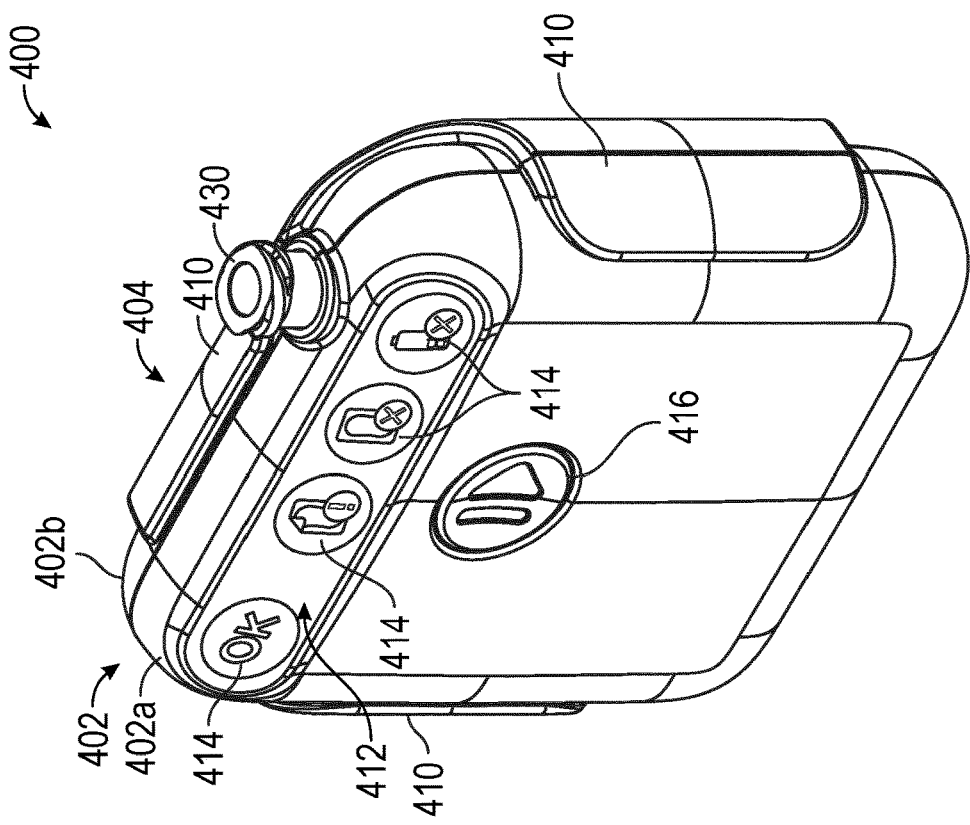
Figure 4C:
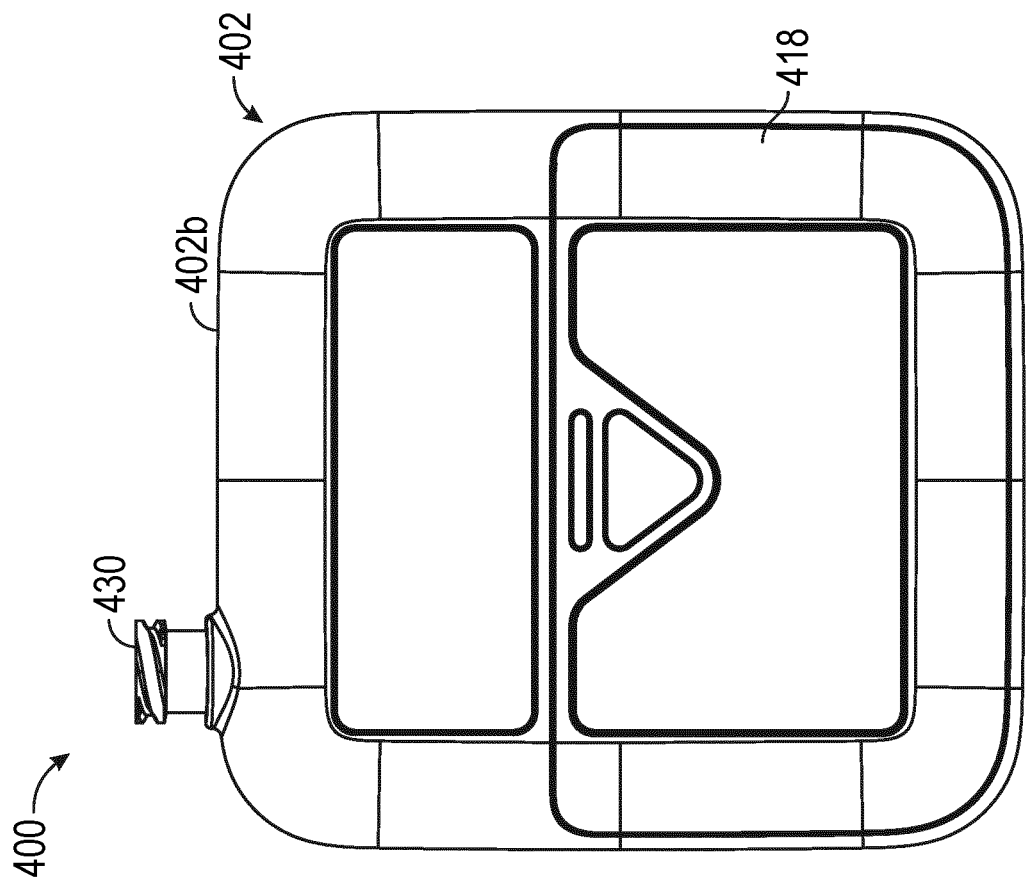

FIGS. 4A-4C illustrate perspective, front, and rear views of a reduced pressure wound therapy device 400. Any arrangements of the device 400 disclosed herein can have any of the features, components, capabilities, or other details of any other arrangements of negative pressure wound therapy devices disclosed herein, including without limitation device 150, in combination with or in place of any of the features, components, capabilities, or other details of the device 400 disclosed herein. For example, the device 400 can be configured to operate in any of the first and/or second operational states as described herein and/or such that any of the visual indicators of the device 400 can emit nonvisible light and/or visible light, or such that any of the visual indicators of the device 400 can emit only nonvisible light in one or more operational states.

The reduced pressure wound therapy device 400 can include a housing 402 and an optional mounting component 410. The mounting component (or attachment) 410 can be removably attached to the housing 402, such that the reduced pressure wound therapy device 400 can be used with or without the mounting component 410. For example, FIG. 4C illustrates the reduced pressure wound therapy device 400 without the mounting component 410. The mounting component 410 can be designed to allow the reduced pressure wound therapy device 400 to be mounted on another object such as, but not limited to, a user's person. The mounting component 410 can include a clip designed to retain the mounting component 410 on a user's outerwear, such as on a user's pocket, a pouch, a belt, a flap, or otherwise.

The housing 402 (sometimes referred to as "outer housing") can contain or support components of device reduced pressure wound therapy device 400. The housing 402 can be formed from one or more portions, such as a front portion 402a and a rear portion 402b, which can be removably attached to form the housing 402.

The housing 402 can include a user interface 412 which can be designed to provide a user with information (for example, information regarding an operational status of the reduced pressure wound therapy device 400). The user interface 412 can include one or more indicators, such as icons 414, which can alert the user to one or more operating or failure conditions of the reduced pressure wound therapy system. For example, the indicators can include icons for alerting the user to normal or proper operating conditions, pump failure, power failure, the condition or voltage level of the batteries, the condition or capacity of a wound dressing, detection of a leak within the wound dressing or fluid flow pathway between the wound dressing and the pump assembly, suction blockage, or any other similar or suitable conditions or combinations thereof. An example set of icons 414 is illustrated in FIGS. 4A-4B which, from left to right, can include an "OK" indicator which can indicate normal operation of the system, a "leak" indicator which can indicate the existence of a leak in the system, a "dressing full" indicator which can indicate that a wound dressing is at or near capacity, and a "battery critical" indicator which can indicate that the power source (such as, one or more batteries) is at or near a critical level. The icons 414 can have a green or orange color, or can be illuminated with a green or orange light (for example, colored LEDs).

In any arrangements disclosed herein, the device 400 can be configured such that the user interface 412 emits light that has a wavelength that is above the wavelength that is visible to the human eye when the device is in one or more operational states, including without limitation the second operational state. In any arrangements disclosed herein, the device 400 can be configured such that the user interface 412 does not emit any visible light when the device is in one or more operational states, including without limitation the second operational state.

The reduced pressure wound therapy device 400 can include one or more user input features, such as button 416, designed to receive an input from the user for controlling the operation of the device 400, including changing an operational state of the device. A single button can be present which can be used to activate and deactivate the reduced pressure wound therapy device or control other operating parameters of the device 400. For example, the button 416 can be used to activate the reduced pressure wound therapy device 400, pause the device 400, clear indicators (such as, one or more icons 414, or be used for any other suitable purpose for controlling an operation of the device 400 (for example, by sequentially pushing on the button 416). The button 416 can be a push style button that can be positioned on an outside, front surface of the housing 402. In some cases, multiple input features (for example, multiple buttons) can be provided.

The reduced pressure wound therapy device 400 can include a connector 430 for connecting a tube or conduit to the device 400. The connector 430 can be used to connect reduced pressure wound therapy device to a wound dressing.

The reduced pressure wound therapy device 400 can be a canisterless device. The wound dressing can retain fluid (such as, exudate) aspirated from the wound. Such a dressing can include a filter, such as a hydrophobic filter, that prevents passage of liquids downstream of the wound dressing (toward the reduced pressure wound therapy device 400).

The reduced pressure wound therapy device 400 can include a removable cover 418, as illustrated in FIG. 4C. The cover 418 can cover a cavity (not shown) in which one or more power sources, such as batteries, for powering the device 400 are positioned.

Additionally or alternatively, in any arrangements disclosed herein, the pump electronics can include one or more digital pressure sensors configured to measure temperature. In some arrangements, the one or more digital pressure sensors can be configured to monitor the combination of patient temperature, external user environment temperature, and/or internal electronic/pump temperature, in real time or otherwise. This can enable the negative pressure wound therapy system to track and forecast excessive temperatures in proximity of parts and components of the pump system such as but not limited to batteries, pump(s), buttons/switches, and/or other electronic components as well as to track and forecast excessive temperatures in the exhaust air of the negative pressure wound therapy system and other fluids or functions of the negative pressure wound therapy system. In some arrangements, if the detected temperature of particular parts, components, fluids (such as patient airflow temperature), or otherwise reach a predetermined threshold temperature level, the pump electronics can be configured to enter a fault mode in which the negative pressure or other functionality of the system is interrupted or otherwise altered. In some arrangements, the predetermined threshold temperature level can be increased for circumstances in which the negative pressure wound therapy system will be exposed to higher ambient temperatures, such as for soldiers using the negative pressure wound therapy system in a desert or other hot environment.

Further, in any arrangements of the negative pressure wound therapy devices or systems disclosed herein, the pump, pump electronics, and/or other electronics can be supported by the wound dressing in what can be referred to as an on-board system. Such arrangements of the negative pressure wound therapy systems can have any of the features, components, capabilities, or other details of any other arrangements of negative pressure wound therapy devices or systems disclosed herein. The pump, pump electronics, and/or other electronics of such on-board systems or other systems disclosed herein can have one or more indicators, including visual indicators, audio indicators, vibratory indicators, or otherwise. Such visual indicators can be configured to be switchable from a first operational state in which the device emits visible light and a second operational state in which the device emits light only nonvisible light.

Any of the negative pressure wound therapy devices described herein can include one or more features disclosed in U.S. Patent Publication No. 2019/0231939, which is incorporated by reference herein in its entirety.

Other Variations

Although some arrangements describe negative pressure wound therapy, the systems, devices, and/or methods disclosed herein can be applied to other types of therapies usable standalone or in addition to TNP therapy. Systems, devices, and/or methods disclosed herein can be extended to any medical device, and in particular any wound treatment device. For example, systems, devices, and/or methods disclosed herein can be used with devices that provide one or more of ultrasound therapy, oxygen therapy, neurostimulation, microwave therapy, active agents, antibiotics, antimicrobials, or the like. Such devices can in addition provide TNP therapy. The systems and methods disclosed herein are not limited to medical devices and can be utilized by any electronic device.

Any of transmission of data described herein can be performed securely. For example, one or more of encryption, https protocol, secure VPN connection, error checking, confirmation of delivery, or the like can be utilized.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, arrangement, or example are to be understood to be applicable to any other aspect, arrangement or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing arrangements. The protection extends to any novel one, or any novel combination, of the features disclosed in this specification (including any accompanying claims, abstract and drawings), or to any novel one, or any novel combination, of the steps of any method or process so disclosed.

While certain arrangements have been described, these arrangements have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some arrangements, the actual steps taken in the processes illustrated and/or disclosed may differ from those shown in the figures. Depending on the arrangement, certain of the steps described above may be removed, others may be added. For example, the actual steps and/or order of steps taken in the disclosed processes may differ from those shown in the figure. Depending on the arrangement, certain of the steps described above may be removed, others may be added. For instance, the various components illustrated in the figures may be implemented as software and/or firmware on a processor, controller, ASIC, FPGA, and/or dedicated hardware. Furthermore, the features and attributes of the specific arrangements disclosed above may be combined in different ways to form additional arrangements, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Conditional language used herein, such as, among others, "can," "could", "might," "may," "e.g.," and the like, unless specifically stated otherwise, or otherwise understood within the context as used, is generally intended to convey that certain arrangements include, while other arrangements do not include, certain features, elements and/or states. Thus, such conditional language is not generally intended to imply that features, elements and/or states are in any way required for one or more arrangements or that one or more arrangements necessarily include logic for deciding, with or without author input or prompting, whether these features, elements and/or states are included or are to be performed in any particular arrangement. The terms "having," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language, such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain arrangements require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain arrangements, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. Although the present disclosure includes certain arrangements, examples and applications, it will be understood by those skilled in the art that the present disclosure extends beyond the specifically disclosed arrangements to other alternative arrangements and/or uses and obvious modifications and equivalents thereof, including arrangements which do not provide all of the features and advantages set forth herein. Accordingly, the scope of the present disclosure is not intended to be limited by the specific disclosures of preferred arrangements herein, and may be defined by claims as presented herein or as presented in the future.

What is claimed is:

1. A negative pressure wound therapy system, comprising:
a housing with an exterior surface;
a source of negative pressure enclosed by the housing, the source of negative pressure configured to aspirate fluid from a wound covered by a wound dressing;
one or more visual indicators visible at the exterior surface of the housing, the one or more visual indicators configured to indicate a status of the system to a user; and
electronic circuitry enclosed by the housing;
wherein:
the electronic circuitry is configured to automatically, or in response to an input from the user, transition between at least a first operational state and a second operational state;
the negative pressure wound therapy system is configured to detect when the visible light surrounding the negative pressure wound therapy system is reduced to below a threshold level and to automatically transition to the second operational state or to continue operating in the second operational state in response to determining that the visible light surrounding the system is below the threshold level; and
in the second operational state, the one or more visual indicators are configured to emit light at one or more wavelengths that are not visible to a naked human eye.

2. The system of claim 1, wherein in the second operational state, the one or more visual indicators are configured to emit light at the one or more wavelengths that are visible to a user using a night vision viewing device.

3. The system of claim 1, wherein in the first operational state, the one or more visual indicators are configured to emit light that is visible to the naked human eye.

4. The system of any of claim 1, wherein in the second operational state, the system is configured to not emit any visible light when the negative pressure wound therapy system is operating.

5. The system of claim 1, wherein the one or more visual indicators are configured to be dimmed based on a level of ambient light.

6. The system of claim 1, wherein the electronic circuitry is further configured to transition between at least the first operational state and the second operational state in response to a single press of a button positioned at least partially on the exterior surface.

7. The system of claim 1, wherein the electronic circuitry is further configured to transition between at least the first operational state and the second operational state in response to manipulation of at least one of a physical or a touchscreen-based button, a switch, a slider, or a dial positioned at least partially on the exterior surface.

8. The system of claim 1, wherein the one or more visual indicators are configured to emit infrared light in the second operational state.

9. The system of claim 1, wherein the one or more visual indicators are configured to emit light only at a wavelength that is 850 nm or greater, 940 nm or greater, or 1000 nm or greater in the second operational state.

10. The system of claim 1, further including one or more audible indicators configured to indicate the status of the system, the one or more audible indicators configured to be silent in the second operational state and configured to provide audible indication in the second operational state.

11. The system of claim 1, further including one or more tactile indicators configured to indicate the status of the system in the second operational state.

12. The system of claim 1, wherein in the second operational state, the system is configured to not transmit any communication data to a remote computing device.

13. The system of claim 1, wherein the system further comprises a collection canister configured to be coupled with the housing, the collection canister being in communication with the source of negative pressure and being configured to collect exudate from a wound.

14. The system of claim 1, wherein the status is related to the configuration, control, and/or operation of the system.

15. The system of claim 1, wherein the electronic circuitry is configured to automatically transition to the second operational state in response to determining that the visible light surrounding the system is reduced to below a threshold level.

16. The system of claim 1, wherein the wound dressing is configured to be fluidically coupled with the source of negative pressure.

17. A negative pressure wound therapy system, comprising:
a housing with an exterior surface;
a source of negative pressure configured to provide a reduced pressure to a space between a wound and a wound dressing;
a light sensor configured to detect or monitor a state of visible light around the negative pressure wound therapy system; and
one or more visual indicators visible at the exterior surface of the housing, the one or more visual indicators configured to indicate a status of the system to a user;
wherein:
the negative pressure wound therapy system is configured such that, in at least one operational state, the one or more visual indicators emit light only at one or more wavelengths that are not visible to the naked eye;

the system is configured to automatically transition to the at least one operational state in which the one or more visual indicators emit light only at one or more wavelengths that are not visible to the naked eye or configured to automatically operate in the at least one operational state in which the one or more visual indicators emit light only at one or more wavelengths that are not visible to the naked eye when the light sensor determines that the negative pressure wound therapy system is surrounded by darkness.

18. A method of operating a negative pressure wound therapy device, comprising:

activating the negative pressure wound therapy device that is coupled with a wound dressing so as to aspirate fluid from a wound covered by a wound dressing;

determining when the visible light surrounding the negative pressure wound therapy device is reduced to below a threshold level; and changing the negative pressure wound therapy device to a second operational state in which one or more visual indicators of the negative pressure wound therapy device emit light only at one or more wavelengths that are not visible to naked human eye but are visible using a night vision device when the visible light surrounding the negative pressure wound therapy device is reduced to below a threshold level, thereby permitting monitoring one or more operating parameters of the negative pressure wound therapy device while the negative pressure wound therapy device is in the second operational state by viewing the one or more indicators using the night vision viewing device;

wherein the device is configured to automatically transition to the second operational state or automatically operate in the second operational state when the visible light surrounding the negative pressure wound therapy device is reduced to below a threshold level.

19. The method of claim 18, wherein the night vision viewing device comprises a pair of night vision goggles or a night vision scope.

20. The system of claim 1, comprising one or more vibratory indicators configured to indicate a status of the system to a user.

21. The system of claim 1, comprising a light sensor configured to detect or monitor a state of visible light around the negative pressure wound therapy system.

* * * * *